United States Patent [19]
Greene

[11] Patent Number: 5,327,881
[45] Date of Patent: Jul. 12, 1994

[54] FIBEROPTIC INTUBATING STYLET

[75] Inventor: Christopher M. Greene, Waltham, Mass.

[73] Assignee: Beth Israel Hospital Association, Boston, Mass.

[21] Appl. No.: 23,073

[22] Filed: Feb. 26, 1993

[51] Int. Cl.$^5$ .............................. A61B 1/00
[52] U.S. Cl. ................................. 128/11; 128/4; 128/10
[58] Field of Search ............... 128/6, 4, 11, 46 M, 128/10, 207.14

[56] References Cited

U.S. PATENT DOCUMENTS

| | | | |
|---|---|---|---|
| 3,669,098 | 6/1972 | Takahashi | 128/6 |
| 3,776,222 | 12/1973 | Smiddy | 128/6 |
| 4,337,761 | 7/1982 | Upsher | 128/11 |
| 4,527,553 | 7/1985 | Upsher | 128/11 |
| 4,577,621 | 3/1986 | Patel | 128/4 |
| 4,742,819 | 5/1988 | George | 128/6 |
| 4,846,153 | 7/1989 | Berci | 128/6 |
| 4,906,230 | 3/1990 | Maloney et al. | 128/4 X |
| 4,911,148 | 3/1990 | Sosnowski et al. | 128/6 |
| 5,005,573 | 4/1991 | Buchanan | 128/207.14 |
| 5,016,614 | 5/1991 | MacAllister | 128/6 X |
| 5,095,888 | 3/1992 | Hawley | 128/10 |
| 5,168,864 | 12/1992 | Shockey | 128/6 X |

*Primary Examiner*—Richard J. Apley
*Assistant Examiner*—Beverly A. Meindl
*Attorney, Agent, or Firm*—Lahive & Cockfield

[57] ABSTRACT

An intubation assisting device includes an elongate stylet having a lens at a distal end thereof, a flexible bellows region proximal to the lens, and a semi-malleable region proximal to the flexible bellows. The stylet is mountable upon a body portion that has a handle mountable thereto. The body and styler have internally disposed therein an optical fiber assembly that enables a physician to view a patient's internal anatomy during an intubation procedure with the aid of an eyepiece disposed at a proximal end of the body portion. A pair of control cables extend within the bellows region of the stylet to the exterior of the device to facilitate articulation of the distal end of the stylet.

17 Claims, 3 Drawing Sheets

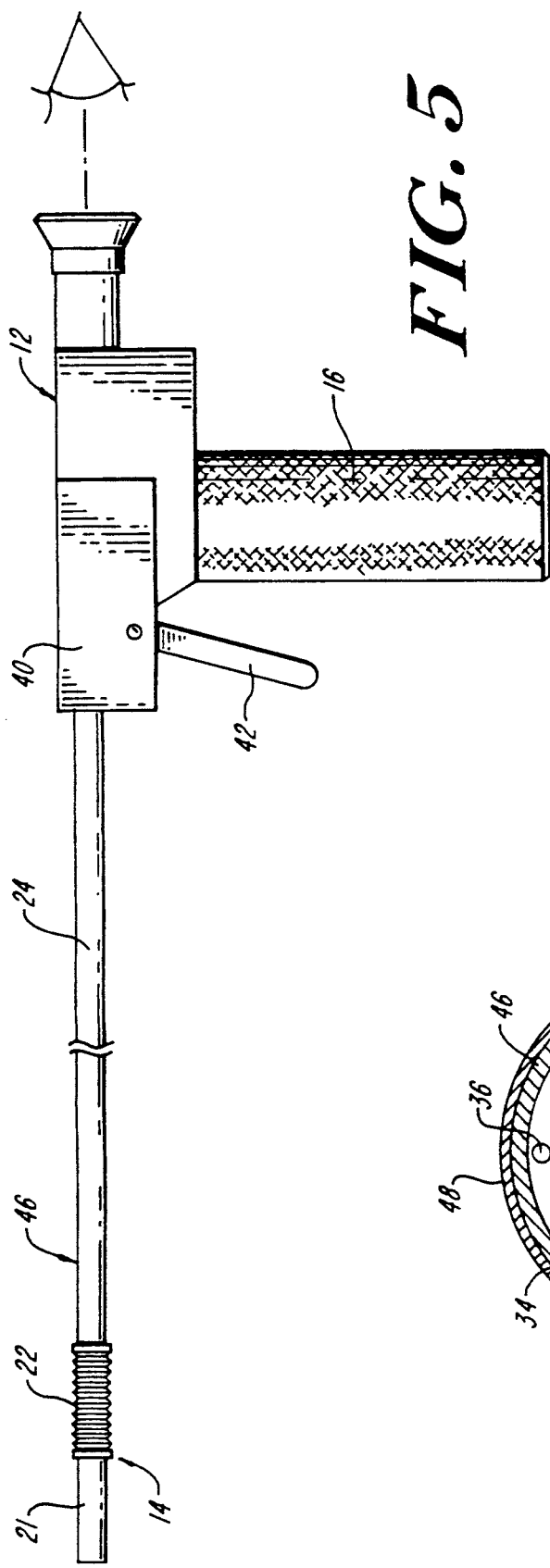
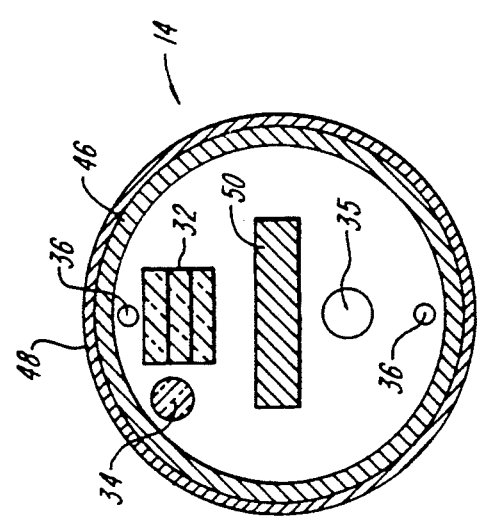

FIBEROPTIC INTUBATING STYLET

BACKGROUND OF THE INVENTION

This invention relates to an intubation device, and more particularly to a fiberoptic stylet which facilitates the placement of an endotracheal tube within the trachea.

During surgery and other medical procedures it is often necessary to insert an endotracheal tube (ET) into the trachea of a patient for the purposes of ventilation assistance, or otherwise. It is sometimes necessary, such as in emergency situations, to position the endotracheal tube rapidly. Failure to properly position the tube, or failure to insert the tube sufficiently quickly, can result in medical complications or even death.

Intubation generally involves placement of an endotracheal tube through a patient's larynx and into the trachea. To do so it is necessary to displace the epiglottis which usually spans the glottic opening into the larynx. Skill and expertise are required to properly intubate a patient. The intubation procedure is even more difficult in situations where, due to a medical condition or anatomical abnormality, it is difficult to visualize the glottis of the patient.

Devices have thus been developed to enable physicians to visualize the pharyngeal area and larynx of a patient during placement of an ET tube. For example, U.S. Pat. No. 4,742,819 discloses a fiberoptic stylet that accommodates an ET tube and displays images on an associated screen. Also, U.S. Pat. No. 3,776,222 discloses a device that enables an ET tube to be inserted through the nasal pharynx while viewing the anatomy of the patient. Other devices that may assist a physician to insert an ET tube while viewing a patient's anatomy are disclosed in U.S. Pat. Nos. 3,669,098; 4,337,761; 4,527,553; and 5,095,888.

Despite the existence of such devices there remains a need for a device which facilitates insertion of an endotracheal tube while viewing a patient's anatomy to ensure proper positioning of the ET tube under both elective and emergency procedures.

Accordingly, it is an object of the invention to provide a device that facilitates the placement of an endotracheal tube within the trachea of a patient while viewing a patient's anatomy. Another object of the invention is to provide such a device having a distal end that is able to be articulated in order to control the positioning of an endotracheal tube. A further object of the invention is to provide such a device that includes a reusable fiberoptic package readily disassembled to facilitate both intubation and servicing of its components. It is also an object of the invention to provide an economical, easy to use device for facilitating placement of an endotracheal tube. Other objects of the invention will be apparent upon reading the disclosure which follows.

SUMMARY OF THE INVENTION

The present invention is directed to a device that assists a physician in placing an endotracheal tube within the trachea of a patient. The device of the invention enables the physician to visualize the pharyngeal area and larynx of the patient during delivery and placement of the endotracheal tube, and to manipulate or flex the tube to assist in its placement. The device is adapted to fit within an endotracheal tube such that the distal end of the endotracheal tube extends slightly beyond the distal end of the intubation assisting device. An optical fiber assembly and lens system disposed within the device enables the physician to visualize a patient's internal anatomy during placement of the endotracheal tube.

While the device may be used by itself, it is designed for singlehanded use so that the operator may use a conventional laryngoscope blade in his free hand to move aside the soft tissue structures of the pharynx, thus optimizing the initial placement of the distal end of the stylet. Although the device is intended to facilitate placement of an endotracheal tube, a variation of the styler equipped with a jet ventilation orifice may be used by itself to oxygenate and jet ventilate the patient when the glottic opening is too narrow to permit placement of the endotracheal tube. The same orifice may also be used to deliver medicaments to a patient.

The intubation assisting device of the invention comprises a handle portion and a light source and a power source, each of which can be disposed on the handle or otherwise associated with the device. A body component is adjacent to and preferably is detachably mountable to the handle component. The body component includes at its proximal end an eyepiece and lens system adjacent to an optical fiber assembly. An intubating stylet can be permanently joined to the body component. Alternatively, the stylet can be removably and replaceably mounted to the body component by mating a stylet base, disposed at a proximal end of the stylet, to the body component.

The stylet is an elongate member that includes a first, semi-malleable portion at the proximal end thereof, a flexible region adjacent to the semi-malleable portion, and a distal end adjacent the flexible region. The semi-malleable portion preferably is formed from a semi-malleable material able to be formed to a desired shape and to retain a desired shape during use of the device. Alternatively, the semi-melleable region can be formed from a flexible outer casing within which is disposed a semi-malleable structure or material. The flexible region, which may be a flexible bellows, is adjacent to the semi-malleable portion and is able to be manipulated, preferably in a vertical plane, to articulate the distal end of the stylet. The flexible region may be directly articulated by an articulation control assembly inside the stylet (i.e., control wires) or may be indirectly controlled by using an endotracheal tube with an articulatable tip, such as the Mallincrodkt "Endotrol" endotracheal tube. The distal end of the stylet includes or consists of a lens device, preferably a self-focusing lens, for facilitating viewing of objects adjacent to the distal end of the stylet.

An optical fiber assembly preferably is disposed within and extends from the body portion of the intubation assembly through the interior of the styler and terminates adjacent the lens device. In addition, an illumination fiber assembly extends from within the interior òf the body component and through the stylet, terminating at a distal portion of the stylet. A light source may be disposed within the handle portion and adapted to communicate light to the illumination fibers. Further, the device includes an articulation control assembly which effects the flexing of the flexible or bellows portion of the stylet during an intubation procedure, and hence articulation of the distal tip.

The device may also be constructed with a hollow channel disposed throughout the length of the styler that terminates at the distal tip, with the proximal end of the device constructed so as to provide a connection for oxygen insufflation, jet ventilation, or drug administration. Oxygen insufflation can improve visibility by removing any secretions that may be adjacent to the distal end of the stylet. Moreover, oxygen insufflation can provide oxygen to the patent even before intubation is effected.

BRIEF DESCRIPTION OF THE DRAWINGS

FIG. 5 is a schematic view of an alternative embodiment of an intubation assisting device constructed according to the present invention.

FIG. 6 is a cross-sectional view of an alternative stylet constructed according to the present invention.

DETAILED DESCRIPTION OF THE INVENTION

Figure 1:
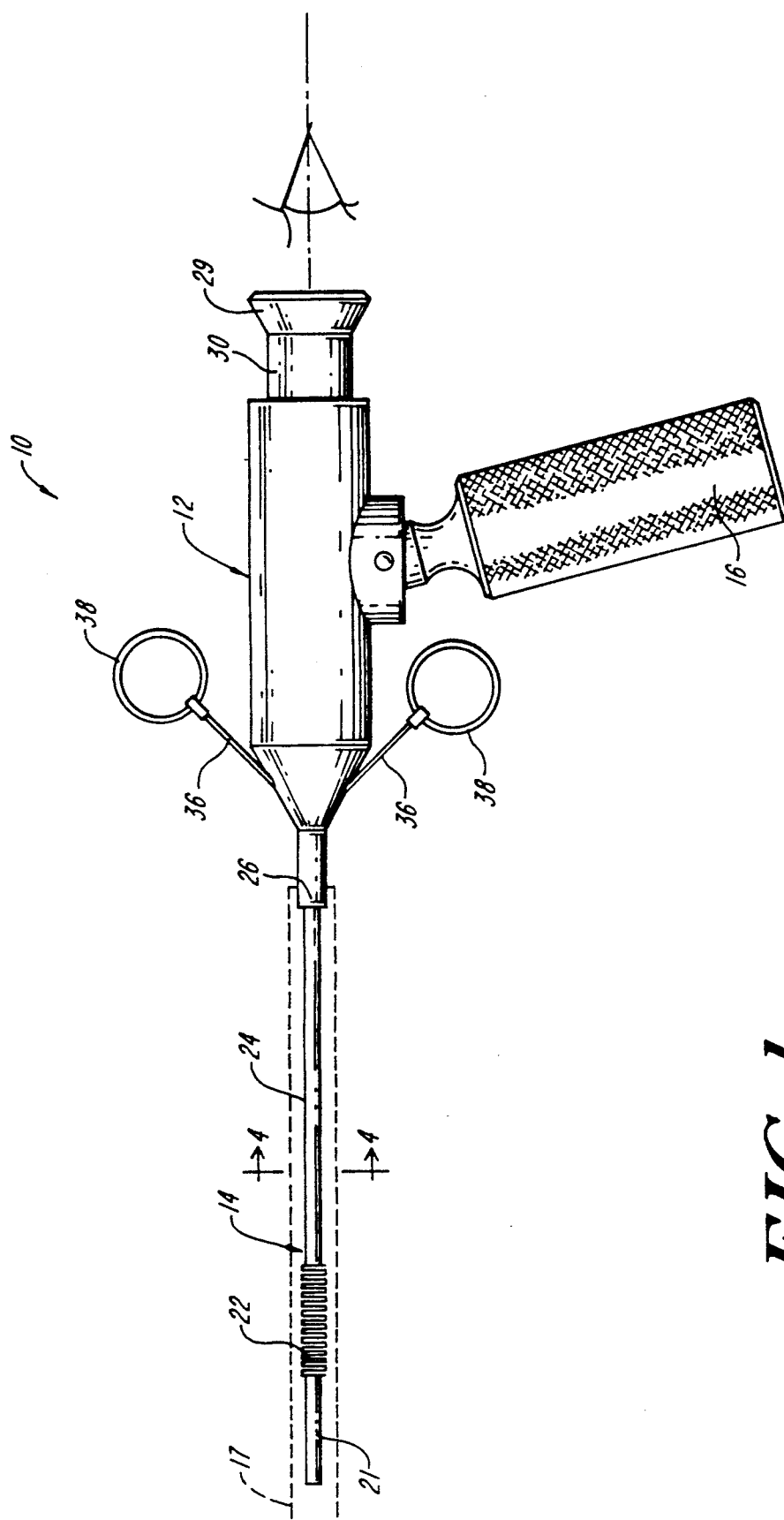
FIG. 1 is a schematic drawing of an intubation assisting device constructed according to the present invention.

The intubation assisting device 10 of the invention facilitates rapid and effective placement of an ET tube within a patient's trachea by allowing direct viewing of the patient's airway during the intubation procedure. Moreover, the distal end of the device may be articulated to control proper positioning of the ET tube. Singlehanded control of this device allows the operator to use a laryngoscope in his or her free hand to further improve vision.

The device 10 features an elongate stylet 14 which extends from a body portion 12 of the device. A handle portion 16 preferably is removably and replaceably attachable to the body portion. The stylet is adapted to fit within a standard endotracheal tube 17, cut to a length such that the distal end of the ET tube extends slightly beyond the distal end of stylet 14.

Figure 3:
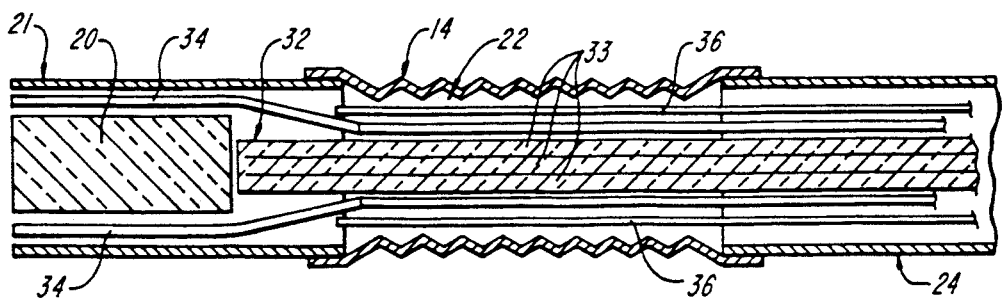
FIG. 3 is a side, sectional view of a forward end of the stylet portion of the intubation assisting device of FIG. 1.
Figure 4:
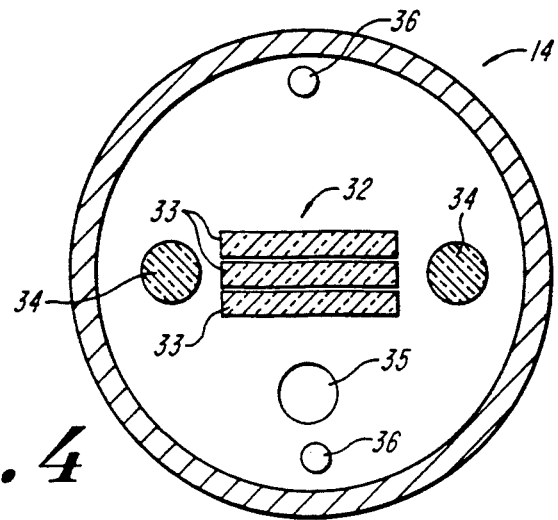
FIG. 4 is a cross-sectional view of the styler of FIG. 1 at lines 4—4.

The stylet 14, as shown in FIGS. 3 and 4, includes within its distal end a lens 20, which preferably is self-focusing. Adjacent and proximal to the distal end is a flexible bellows region 22. An elongate semi-malleable region 24 is disposed adjacent and proximal to region 22. Flexible optical fibers and illuminating fibers, which are described below, are disposed within the styler and the body of the device to enable direct viewing by the operator during the intubation procedure.

As further illustrated in FIG. 1, the styler 14 is placed within a standard ET tube 17 (shown in phantom). An interference ring 26, or a similar region of increased diameter, can be disposed at a proximal end of stylet 12 to provide a slight interference fit with the ET tube to enable it to remain in place on the stylet during intubation. In a preferred embodiment, the stylet is either coterminus with the ET tube, or it terminates a short distance (e.g., about 5-10 mm) prior to the distal end of the ET tube.

Figure 2:
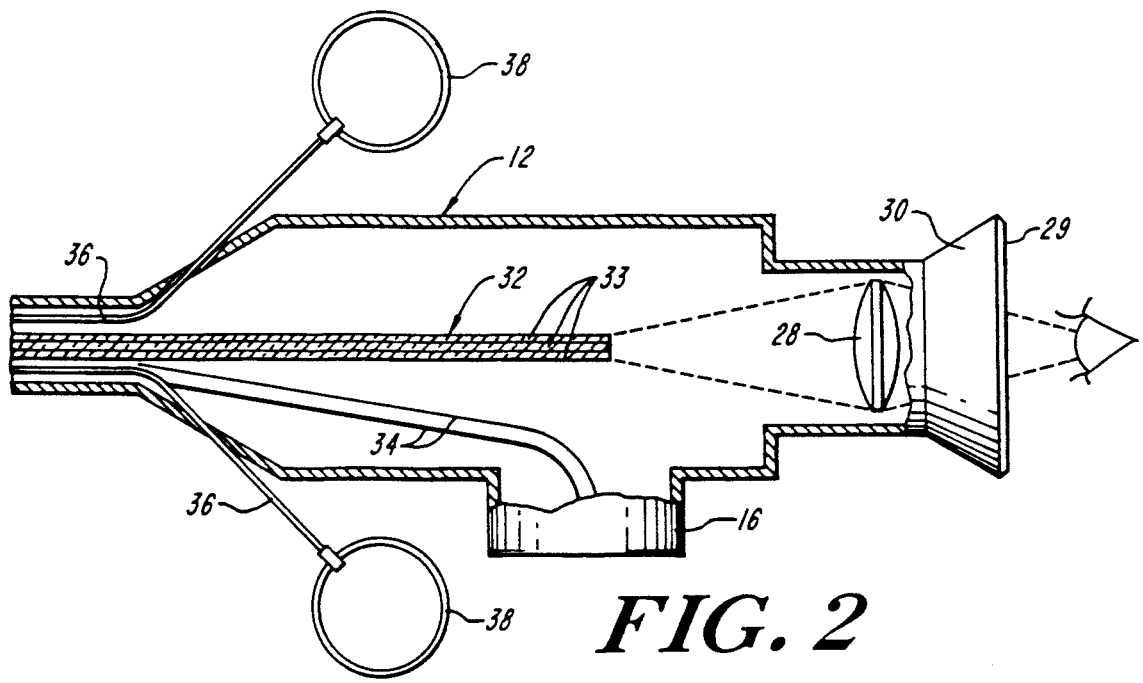
FIG. 2 is a side, sectional view of a body portion of the intubation assisting device of FIG. 1.

FIGS. 2 through 4 also illustrate that interior regions of the body 12 and stylet 14 include an optical fiber package 32, which includes individual optical fiber bundles 33, approximately centrally disposed within the stylet. Preferably, two illuminating fibers 34 are disposed within the body 12 and stylet 14. The illumination fibers 34 are typically positioned with one on either side of the optical fiber package 32. Further, control wires 36 can be disposed within the styler, extending from a point of attachment within the distal end of the flexible region 22 and terminating with control rings 38 that are disposed outside of the stylet and the body.

The stylet 14 may also be constructed with a hollow channel 35 on one side of the optical fiber package 32, extending from its opening on the distal tip of the stylet 14 to a connection orifice on the proximal end of stylet 14. Such a channel is useful to oxygenate or jet ventilate the patient or to deliver medicaments to a patient. The connection orifice may be connected to a source of air or oxygen as will be readily understood by one of ordinary skill in the art.

The proximal end of the body includes an eyepiece 29, and focusing ring 30 to facilitate viewing of objects with the device.

The intubation assisting device of the invention offers several advantages which facilitate safe and effective intubation. Intubation is obviously made easier by the optical capabilities of the device since the physician is able to directly view the patient's airway during the placement of the ET tube. Further, the flexible region of the styler enables the distal end of the styler to be articulated by manipulating control wires 36. This is advantageous as articulation of the styler tip will influence bending of the ET tube and enable it to be easily placed in a desired location. Alternatively, the stylet may be articulated through the use of an endotracheal tube equipped with control cables. In this embodiment bending of the ET tube will influence any necessary articulation of the stylet. An example of a suitable ET tube is the "Endotrol" endotracheal tube available from Mallincrodkt. The semi-malleable region of the stylet that is disposed adjacent and proximal to the flexible region can be bent to a desired shape prior to an intubation procedure and will retain its shape during intubation. The optical fibers disposed within the device continue to provide direct viewing capability despite articulation of the tip or bending of the styler.

As illustrated in FIGS. 2 through 4, the optical fiber package originates within the body 12 of the device and extends through the stylet 14, terminating just prior to the self-focusing lens 20. Likewise, illuminating fibers 34 preferably originate within the body portion 12, and extend through the interior of the body 12 and through the interior of stylet 14. The illuminating fibers 34 preferably terminate at the distal end of the stylet adjacent lens 20. Although the use of two illuminating fibers is preferred, it is understood that one may choose to use only one or more than two such illuminating fibers.

In a preferred embodiment the device includes at least two articulation control wires 36 which extend from a point of attachment within the distal end of the flexible region 22 through the interior of the stylet 14, and emerge from the proximal end of the stylet 14. Control wires 36 may terminate with a mechanism that enables control of the wires, such as control rings 38. Control wires 36 are ideally positioned opposite each other such that they may impart opposed flexing forces to flexible region 22. Manipulation of the control wires 36 by a mechanism such as control rings 38 enables a bending force to be delivered to the bellows 22, causing articulation of the distal tip of the stylet 14. Preferably the control wires 36 attach at the distal end of bellows 22 adjacent lens 20.

Other mechanisms may also be used to impart flexing forces to flexible region 22. For example, as shown in FIG. 5, a trigger mechanism 42 may communicate with a control wire (not shown) that attaches at a distal end of flexible region 22. Flexible region 22 may be biased to a flexed (e.g., slightly inclined) position or to a horizontal position such that activation of the trigger 42 overcomes the biasing force to impart flex to region 22, and thus to articulate the tip of stylet 14 and ET tube 17. It is also possible to impart flexing forces through the use of a metal guide wire which reversibly flexes or extends given the presence and direction of electrical current flowing through the wire.

The handle 16 preferably includes a power source, such as a rechargeable battery (not shown), and an illumination source (not shown). Activation of the illumination source will communicate light through the illumination fibers and eventually through the lens 20 at the distal end of the styler 14. The handle can be cylindrical in shape with dimensions suitable for the intended use of the device. Preferably, the handle 16 has a length of about 7 cm to 13 cm and a diameter of about 2.5 cm to 4.5 cm. It is also possible to use handle components of other shapes and sizes, such as square or rectangular. In a preferred embodiment, the handle is a standard device which is removably and replaceably mountable upon the body of the device. An exemplary, commercially available handle is the Welch Allyn Model 60815 short laryngoscope handle for use with a light source. One or more switches (not shown) for activating the power source preferably can be mounted upon handle 16.

As illustrated in FIGS. 1 and 2, the body 12 of device 10 includes at its proximal end an eyepiece 29, a focusing ring 30, and a lens 28 which all are adapted to cooperate with optical fiber package 32 to enable viewing of objects. Preferably, a single lens is disposed within the eyepiece, having a magnification of about 4 power. This lens typically has a diameter of approximately 1 inch and a focal length of about 2.5 cm, but it is understood that lenses of other dimensions and sizes may be used as well.

In the embodiment illustrated in FIGS. 1 and 2, the body 12 is integral with the stylet 14. In an alternative embodiment, illustrated in FIG. 5, the body 12 and styler 14 form separate removable and replaceable components. In this alternative embodiment, the proximal end of styler 14 includes a stylet base 40 which is easily mountable in a removable and replaceable manner. A variety of mechanisms suitable for mating styler base 40 with body portion 12 are well known in the art. Preferably, the distal end of the body 12 connects with the stylet 14 by a bayonet-type connection so as to facilitate stylet refurbishing as well as styler interchangeability.

Although the dimensions of the body can vary, the length of the body, from the eyepiece to the beginning of styler 14 is approximately 8 to 12 cm. The width of the body is in the order of about 2 to 3 cm, while the height of the body is in the order of about 3 to 8 cm. One of ordinary skill in the art will readily appreciate the most desirable dimensions for the device of the invention.

As noted above, the internal components of stylet 14 include, from distal end to proximal end, a lens 20, an optical fiber package 32, illumination fibers 34, and articulation control wires 36. The stylet preferably has a length of approximately 26 cm from the distal end of the self-focusing lens to its point of attachment to body 14. Ideally, the length of the stylet is such that when an endotracheal tube is positioned over the stylet, as shown in FIG. 1, the distal end of the stylet does not protrude from the endotracheal tube. The outside diameter of the styler is in the range of approximately 5 to 6.75 mm. Standard endotracheal tubes have an inside diameter of approximately 7 mm and the stylet is designed so that throughout a predominant portion of its length, the outside diameter of stylet 14 is smaller than the inside diameter of the endotracheal tube. This facilitates effortless positioning of the endotracheal tube on the stylet, and easy removal of the tube from the styler. The styler may include at its proximal end an interference ring 26 that has a diameter slightly larger than that of the other portions of the styler. The interference ring 26 facilitates a slight interference fit between the stylet and the proximal end of the endotracheal tube during the intubation procedure.

The lens 20, preferably is a self-focusing lens. In a preferred embodiment lens 20 has a diameter of approximately 3 mm and a large depth of field. Although a large depth of field is preferred, it is also possible to use a lens having a small depth of field. The preferred focal length of such a lens is in the order of approximately 3–10 mm. The preferred depth of field is approximately 4 mm to 50 mm. A suitable self-focusing lens is the SELFOC lens commercially available from Nippon Sheet Glass.

The lens 20 typically is disposed within a tip assembly 21, which preferably is made of stainless steel. The tip assembly 21 and flexible region 22 preferably are permanently attached to one another by soldering, using a medical grade solder, or more preferably, by use of a medically acceptable adhesive such as epoxy. Alternatively, the tip assembly 21 can be securely mounted to styler 14 by disposing it adjacent flexible region 22 within an outer plastic housing formed on the outer wall of stylet 14. Distal portions of the illumination fibers may also be accommodated within the tip assembly 21.

In one embodiment the flexible region 22 of stylet 14 can take the form of a flexible bellows. The bellows should be of sufficient flexibility to enable about 2 cm of movement upwardly and downwardly to facilitate approximately a 45° to 60° field of vision. The bellows forming region 22 is preferably made of nickel or a suitable nickel alloy. Other medically accepted materials may also be used for the bellows, such as certain plastics and/or rubber materials.

The length of the flexible region 22 can range from approximately 0.25 to 8.0 cm, and like the remainder of the styler can have a diameter in the range of 5 to 6.75 mm. The flexible region 22 can be joined at its proximal end to the semi-malleable segment of the stylet by an adhesive such as epoxy or by other means such as by soldering with a medically compatible solder. Alternatively, the flexible region 22 may be securely fitted within a plastic housing forming the outer wall of stylet 14.

As noted above, the articulation control wires 36 are preferably secured at a distal end of the flexible region 22 and extend through the stylet where they emerge from the proximal end of the stylet and terminate in articulation control rings 38. The control wires 36 can be constructed of nylon coated stainless steel, and have a diameter of approximately 0.5 mm. The terminal ends of the control wires 36 are affixed to the distal end of the flexible region 22 by an adhesive such as epoxy. Preferably, the control wires are positioned opposite each other within the outer periphery of the flexible region 22.

In one embodiment, the proximal end of stylet 14 may comprise a semi-malleable region 24 which is formed from a semi-malleable material such as annealed stainless steel or annealed brass. A requirement of the semi-malleable section is that it be able to bend to a desired position, and to remain in that position during an intubation procedure.

In another embodiment, illustrated in FIG. 6, the proximal end of stylet 14 comprises a length of flexible stainless steel monocoil 46 that is encased within a plastic housing 48. Preferably, the plastic housing 48 extends the length of the device and has a thickness of about 0.5 mm. The monocoil preferably has an outside diameter of about 6 mm and an inner diameter of about 5 mm. The proximal end of the stylet can be rendered semi-malleable and able to retain a desired shape by inserting within the monocoil a length of rectangular high carbon, fully annealed steel spring stock 50. The spring stock preferably extends the length of the monocoil and has dimensions of approximately 1.6×4.1 mm. The distal end of the spring stock can be attenuated to a smaller dimension and be cold-soldered to the tip assembly 21 to allow easy flexion of the tip.

The optical fiber package or assembly 32 preferably includes between 1 and 5, and most preferably 3, separate optical fiber bundles. Each bundle typically is rectangular in shape and they are stacked adjacent one another. The dimension of each bundle is approximately 0.5 mm to 2.0 mm in width, depth, and/or diameter. The fiber optic bundles can be made of plastic or glass fiber optic cable.

The illumination fibers 34 disposed adjacent the optical fiber package are coterminus with the self-focusing lens 20. These fibers may be comprised of plastic or glass, and preferably have a diameter of about 0.020 inches. Suitable fibers are commercially available from numerous sources. The illumination fiber assembly 34 may comprise a single fiber or more than one fiber.

The intubation assisting device of the invention may be used as follows. Prior to intubation a standard endotracheal tube, modified to have a length of approximately 26 cm is disposed over stylet 14 as shown in FIG. 1. Thereafter, the physician may intubate a patient by using this device singlehandedly (or in conjunction with a laryngoscope) to flex and/or extend the distal tip of an endotracheal tube while directly viewing the glottis and vocal cords of the patient from the eyepiece of the device. Placement of the endotracheal tube through the vocal cords and into the trachea will be greatly facilitated by such a view, as well as by the fact that the stylet need not extend distal to the ET tube, thus preventing the ET tube from becoming caught on the soft tissues of the trachea as it is advanced off the stylet. A hollow channel that may be included within the stylet portion would allow for oxygen insufflation and/or suctioning while intubating, and would also allow the device to be used for jet ventilation of the patient should an ET tube not be available or otherwise contraindicated. The hollow channel may also be useful for drug administration.

It is understood that various modifications may be made the present invention without departing from the intended scope thereof.

What is claimed is:

1. An intubation assisting device, comprising
   a handle means for manipulating the device;
   a light source and a power source associated with the device;
   a body component, adjacent to the handle means, including at a proximal end thereof an eyepiece and lens system;
   an intubation assembly adjacent to the body component and including an elongate stylet having a diameter enabling it to be disposed within an endotracheal tube, the stylet comprising, at a proximal end thereof, a first, semimalleable or flexible portion able to be formed to a desired shape and to retain a desired shape during use, an intermediate, flexible region adjacent and distal to the first portion, and a third, distal, non-flexible portion of the stylet adjacent the flexible region, having disposed therein a lens means for facilitating viewing;
   a flexible optical fiber assembly disposed within the intubation assembly and terminating adjacent the lens means;
   an illumination fiber assembly disposed within and extending the length of the intubation assembly; and
   a guide means for controlling the flexion of the flexible region of the stylet.
2. The device of claim 1 wherein the flexible region of the stylet comprises a flexible bellows.
3. The device of claim 2 wherein the flexible bellows is manufactured from a material selected from the group consisting of nickel, rubber and elastomer.
4. The device of claim 2 wherein the length of the flexible bellows is approximately 0.25 to 8.0 cm.
5. The device of claim 4 wherein three optical fiber bundles form the optical fiber assembly.
6. The device of claim 5 wherein each optical fiber has dimensions of about 0.5 to 2.0 mm in width, depth and/or diameter.
7. The device of claim 5 wherein the optical fibers are formed of plastic or glass fibers.
8. The device of claim 1 wherein the lens means disposed at the distal tip of the stylet is a self-focusing lens system.
9. The device of claim 1 wherein the illumination fiber assembly comprises at least one light transmitting flexible fiber.
10. The device of claim 1 wherein the guide means comprises control wires which extend within the interior of the intubation assembly, each wire having a distal end secured to opposed surfaces of the distal end of the flexible region of the stylet and a proximal end secured to a control mechanism positioned on the exterior of the device and adapted to provide a flexing force to the flexible bellows upon manipulation thereof.
11. The device of claim 10 wherein the control wires communicate with a trigger mechanism, manipulation of which results in flexion of the flexible region of the styler.
12. The device of claim 10 wherein the control wires terminate with control rings, manipulation of which results in flexion of the flexible region of the stylet.
13. The device of claim 1 wherein the flexible region of the stylet comprises an annealed, flexible metal segment.
14. The device of claim 1 wherein the light and power source are associated with the handle means.
15. The device of claim 1 wherein the body component is detachably mountable to the handle means.
16. The device of claim 1 further including a hollow channel disposed within and extending through the stylet, the channel communicating with a connection orifice at the proximal end of the stylet and an opening at the distal end of the styler.
17. The device of claim 16 wherein the hollow channel is suitable for the delivery of medicaments, oxygenation, and jet ventilation.

* * * * *